(12) United States Patent
Schausberger et al.

(10) Patent No.: US 8,222,615 B2
(45) Date of Patent: Jul. 17, 2012

(54) DATA ACQUISITION METHOD USING A LASER SCANNER

(75) Inventors: Alois Schausberger, Salzburg (AT); Andreas Gfrörer, Königsdorf (DE); Wolfgang Fuchs, Salzburg (AT)

(73) Assignee: Tecan Trading AG, Mannedorf (CH)

( * ) Notice: Subject to any disclaimer, the term of this patent is extended or adjusted under 35 U.S.C. 154(b) by 97 days.

(21) Appl. No.: 12/666,035

(22) PCT Filed: Feb. 13, 2009

(86) PCT No.: PCT/EP2009/051689
§ 371 (c)(1), (2), (4) Date: Sep. 7, 2010

(87) PCT Pub. No.: WO2009/103663
PCT Pub. Date: Aug. 27, 2009

(65) Prior Publication Data
US 2011/0006219 A1    Jan. 13, 2011

(30) Foreign Application Priority Data
Feb. 21, 2008  (DE) .......................... 10 2008 010 435

(51) Int. Cl.
*G01J 1/58*    (2006.01)
(52) U.S. Cl. .................................................. 250/459.1
(58) Field of Classification Search .................. 250/234, 250/458.1, 459.1; 359/368, 385
See application file for complete search history.

(56) References Cited

U.S. PATENT DOCUMENTS

| | | | |
|---|---|---|---|
| 5,283,433 A | 2/1994 | Tsien | |
| 5,304,810 A | 4/1994 | Amos | |
| 5,668,887 A | 9/1997 | Parker et al. | |
| 2006/0056015 A1 | 3/2006 | Nishiyama | |

FOREIGN PATENT DOCUMENTS

| | | |
|---|---|---|
| DE | 691091 | 8/1995 |
| DE | 68924460 | 6/1996 |
| DE | 69030703 | 9/1997 |
| DE | 10041165 | 3/2002 |
| DE | 10126286 | 12/2002 |
| DE | 102005037570 | 2/2006 |
| DE | 112004001972 | 8/2006 |
| DE | 102005045163 | 3/2007 |
| DE | 102005047218 | 4/2007 |
| DE | 102006025445 | 12/2007 |
| EP | 0176358 | 4/1986 |
| EP | 0380077 | 8/1990 |
| EP | 0845693 | 6/1998 |
| EP | 0871052 | 10/1998 |

(Continued)

*Primary Examiner* — Mark R Gaworecki
(74) *Attorney, Agent, or Firm* — Notaro, Michalos & Zaccaria P.C.

(57) ABSTRACT

Method has laser scanner for pixel-precise imaging of fluorescent samples having fluorescent dyes. The scanner has sample table, laser and first optical system providing laser beam for exciting the samples, scanner head with deflecting element for scanning sample, first lens, second optical system for forwarding emission beams triggered by the laser beam and deflected by first lens and deflecting element to a detector, position encoder emitting position signals indicating location of the scanner head, electronic element for filtering the detector signals with a time constant and an A/D converter for digitizing the filtered detector signals. The filtered detector signals and the position encoder signals are acquired independently, in parallel and continuously by a computer and are related to a common time base, the A/D conversion being carried out often so that each pixel of an image is always assigned more than one data point.

19 Claims, 5 Drawing Sheets

FOREIGN PATENT DOCUMENTS

| | | |
|---|---|---|
| EP | 1209504 | 5/2002 |
| EP | 1291627 | 3/2003 |
| EP | 1767979 | 3/2007 |
| GB | 2184321 | 6/1987 |
| JP | 2003043369 | 2/2003 |
| JP | 2004144734 | 5/2004 |
| WO | WO 0173374 | 10/2001 |
| WO | WO 02/059677 | 8/2002 |
| WO | WO 2007/101205 | 9/2007 |

DATA ACQUISITION METHOD USING A LASER SCANNER

The invention relates to a data acquisition method using a laser scanner for imaging and/or measuring fluorescent samples which are located on slides and have been treated using fluorescent pigments. A laser scanner suitable for use with the data acquisition method according to the invention comprises a sample table having a receptacle for slides in a sample plane; at least one laser and a first optical system for providing at least one laser beam for exciting the fluorescent samples; a motor-driven scanner head, which moves nonlinearly in space, having an optical deflection element for deflecting the laser beams toward the sample and for scanning this sample in at least one movement direction; a first objective for focusing the laser beams on the sample in the plane; a second optical system for relaying emission beam bundles, which are triggered by the laser beams on the sample and are deflected through the first objective and the deflection element, to at least one detector; a position encoder, which emits position encoder signals, which indicate the instantaneous whereabouts of the scanner head in relation to a zero point; an electronic element for filtering detector signals of the detector using a defined time constant; and an A/D converter for digitizing the filtered detector signals.

For some time, conventional optical scanning microscopes have been used for imaging fluorescent samples located on slides. Confocal optical scanning microscopes are being used ever more frequently because of the improved resolution. Such a microscope is known, for example, from GB 2 184 321 A. This microscope conducts the light of a laser source along an optical path, in order to scan a sample located in the object plane of the microscope using the focused light beam. The fluorescent beam emitted by the sample is conducted back through the same optical path for de-screening, separated from the excitation beam using a dichroic mirror, and imaged on the confocal opening in front of a detector. An image is thus formed from the fluorescence of a sample, without the light directed onto the sample to trigger the fluorescence being able to hit the detector.

Many commercially available microscopes are based on this design and have beam splitters or filters for dividing the light emitted from the sample into beams having different wavelength ranges. Two fluorescent pigments may thus also be used and their emission may be measured using two different detectors.

However, all confocal scanner systems which conduct the two excitation beams having the two different wavelengths onto the same scanning spot have the disadvantage that the two emission signals can only be delimited spectrally. Because the absorption and/or the fluorescence emission spectra of the pigments used typically overlap, they may not be reliably and quantitatively differentiated (in particular in the event of greater intensity differences). In order that first one image having a first fluorescence spectrum and then a second image using another type of the excitation beam do not have to be generated in a time-consuming way, scanning microscopes and "scanners" have been proposed which provide at least two excitation beams having different orientations.

Such a microscope is known, for example, from U.S. Pat. No. 5,304,810, which generates two or more spatially separate illumination points using two or more spatially separate illumination beams and scans a sample simultaneously using these illumination points. The fluorescence emission beam bundles which are thus simultaneously generated and are spatially separated from one another are simultaneously measured using individual detectors oriented on these spatially separated illumination points. Such a microscope is also known from U.S. Pat. No. 6,628,385 B1, which generates two separate light spots on a sample using two excitation lasers. The two excitation beams penetrate an opening in a 45° mirror at slightly different angles and are then incident on an objective element. This causes the provision of two separate light spots on the sample, an emission beam bundle being generated at each light spot. The two resulting emission beam bundles are reflected on the 45° mirror and are incident on a secondary lens, after which they each reach one of two detectors directly or after a second deflection. In addition, optical separation elements, such as dichroic filters or prisms, may be positioned in front of the detectors, which are implemented as photomultipliers. A scanning system situated between the 45° mirror and the objective element can be used for scanning the samples.

An optical system for exciting and measuring fluorescence on or in samples treated using fluorescent pigments is known from WO 02/059677 A1. This system comprises at least one laser for exciting the fluorescent pigments used, a mirror for deflecting the laser light in the direction of a sample, a deflection element for deflecting the light from the laser onto this mirror in a Y direction of a coordinate system (Cartesian here), optics for forming a first focal point of the laser light on the sample, a scanning unit, which comprises the mirror and the optics and is movable in the Y direction, a sample table, which is movable in the X and Z directions of the coordinate system, for orienting the sample relative to the first focal point, an optical configuration for imaging the light emitted from the sample in an aperture plate situated in a second focal point and a detector for measuring the intensity of the light passing through the aperture plate.

These known microscopes for the high-sensitivity scanning of samples situated in a regular pattern (a so-called array) are additionally capable of scanning an entire standard slide for light microscopy and operate satisfactorily at moderate resolution. However, it is to be noted that upon increase of the resolution, additional effects such as dynamic shifts between the color channels may become visible. Therefore, for example, the pixels of the red and green channels no longer lie precisely one above another. The relative shift can change dynamically between the channels over the extent of the image. In addition, this shift is substantially a function of the positioning precision of the sample in the focus. For these reasons, a relative shift is only correctable later by software with great difficulty.

If the two channels are to be separated from one another not only spectrally, but rather also spatially, the two focal points of the excitation lasers on the sample must be separated from one another. This may only be achieved in that the bundled light beams of the two lasers are incident on the scanning objective at a small but significant angle to one another. It is generally known that all beams incident on the objective at a specific angle are focused on the same point within the focal plane. A specific angle of incidence in front of the objective thus always corresponds to a specific location behind the objective. In this context, it is unimportant whether the laser beam is incident on the objective in its center or in any other subarea of the objective aperture; the bundling in the same focal point is not affected thereby. However, the beam angle behind the objective is different, and the beams are now incident in the focal point together from different directions. In the exact focal point, this does not play a role, but it does in planes which lie slightly above or below it. The beams thus move away from the exact focal point at different speeds as a function of this angle.

If two laser beams are focused on one sample and spatially separate from one another in the focal plane in accordance with these conditions and if these laser beams therefore form an angle to one another upon incidence on the scanning objective, this automatically has the result that at least one of the two laser beams can also no longer run exactly parallel to the scanning axis before being incident on the mirror element.

If the scanner head is moved, the point of incidence of the laser beam on the objective changes. The beam is still deflected onto the same focal point, but at different angles. As described above, different positions result outside the focal plane depending on the location of the scanner head in the X direction and depending on the deviation of the sample plane from the exact focal plane in the Z direction. The latter deviation can never be entirely prevented in the context of realistic device tolerances and also cannot be monitored as well as desired, like random tolerance.

The described effects are small per se, but are significantly noticeable in the exemplary construction at resolutions below 5 μm. The described effects may have the result that the images of the two detection channels are not congruent over the entire image area, and the extent of the deviations varies in an uncontrolled manner over the image. Quantitative measurements of very small structures thus become impossible or at least corrupted. The errors are visually noticeable as locally varying color seams.

The object of the present invention comprises proposing an alternative data acquisition method for imaging fluorescent samples, which are located on slides and treated using fluorescent pigments, using a laser scanner, using which the sensitivity of the laser scanner is additionally improved.

This object is achieved by a data acquisition method using a laser scanner for the pixel-precise imaging of fluorescent samples, which are located on slides and treated using fluorescent pigments, which comprises the features of independent claim 1. A laser scanner capable of performing this data acquisition method comprises:

a) a sample table having a receptacle for slides in a sample plane;
b) at least one laser and one first optical system for providing at least one laser beam for exciting the fluorescent sample;
c) a motor-driven scanner head, which moves nonlinearly in space, having an optical deflection element for deflecting the laser beams toward the sample and for scanning this sample in at least one movement direction;
d) a first objective for focusing the laser beams on the sample in the plane;
e) a second optical system for relaying emission beam bundles, which are triggered by the laser beams on the sample and are deflected by the first objective and the deflection element, to at least one detector;
f) a position encoder, which emits position encoder signals, which indicate the instantaneous whereabouts of the scanner head in relation to a zero point;
g) an electronic element for filtering detector signals of the detector using a defined time constant; and
h) an A/D converter for digitizing the filtered detector signals.

The data acquisition method according to the invention is characterized in that the filtered detector signals of the A/D converter and the position encoder signals are acquired independently, in parallel, and continuously by a computer unit and/or a controller and are related to a shared timebase, the A/D conversion being performed so frequently that more than one data point of the A/D converter is always associated with each pixel of an image.

Additional preferred embodiments and features according to the invention result from the dependent claims.

Advantages of the data acquisition method according to the invention comprise:

The actual data acquisition time is identical to the total scanning time available due to the continuous data acquisition. This means that 100% of the incoming signals, in particular the incident photons, are also acquired. Therefore, there are no gaps or dead times in which the data acquisition cannot register incident signals. This is in contrast to the typical systems, which use actively switched integrators and whose actual integration time is always reduced by the erasing time. The erasing time is dispensed with in the presented method, all incident photon signals are acquired without gaps. This higher acquisition rate means a higher sensitivity of the system, because it is a direct function of the total number of the acquired photon signals in accordance with the laws of photon statistics.

In the typical approach, the beginning of the integration time is triggered by the sequential position encoder signals. This has the result that it must always be ensured that integration time and erasing time are always fully completed before the following trigger pulse is incident. Because the position encoder signals have a significant "jitter" (instability) (up to ±30%), the fixed integration interval can be at most as large as the smallest possible interval between two trigger signals of the position encoder. Therefore, up to 30% of the actual available measuring time is in turn lost in the conventional methods. In contrast thereto, the method according to the invention completely exploits the duty cycle (operating cycle), which in turn results in increased sensitivity.

Because position encoder signals and data acquisition are recorded independently of one another, the settable pixel resolution of the system is freely scalable and is independent of the position encoder partition, as is the case in conventionally operated systems.

Because at least two raw data points are used per pixel, a filter having a smaller integration constant can be used. The decay behavior between two sequential pixels is thus accelerated and better resolution results at strong light/dark transitions.

The data acquisition method according to the invention using the laser scanner preferred for this purpose will be explained on the basis of schematic drawings, which are not to restrict the scope of the present invention and which only show examples of particularly preferred embodiments. In the figures:

FIG. 3 shows vertical views of the slide magazines with open test object magazine, FIG. 3A showing the insertion side of the two slide magazines in a frontal view seen from the object table, and FIG. 3B showing the two slide magazines in vertical section looking toward the object table;

FIG. 4 shows vertical partial sections through the object table and its transverse inclination device:

FIG. 7 shows a schematic sketch of the scanner head:

FIGS. 11-15 show diagrams of proposed solutions, in which the signal integration (I) is shown as a function of time (t);

Figure 1:
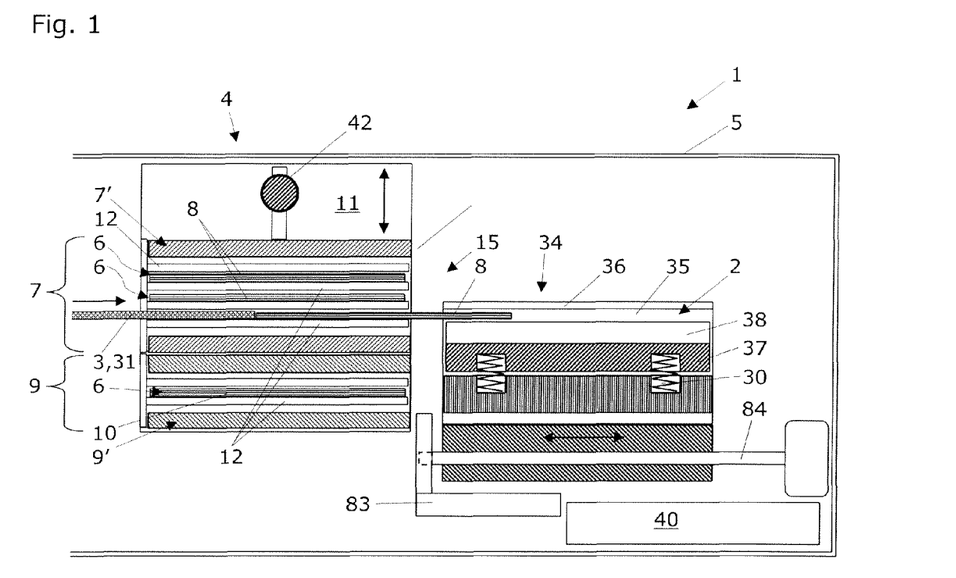
FIG. 1 shows a vertical partial section through two slide magazines and an object table placed in front of them upon transfer of a slide from the sample magazine onto the object table.

FIG. 1 shows a vertical section through two slide magazines and an object table placed in front of them upon transfer of a slide from the sample magazine onto the object table. These two slide magazines are part of a laser scanner 1 according to the invention for imaging and/or measuring fluorescent samples, which are located on slides and treated using fluorescent pigments. This laser scanner comprises a sample table 2, which defines a sample plane 49, and a motorized transport device 3 for moving a slide from a storage unit 4 to the sample table 2 and back. The storage unit 4 comprises one sample part 7 for sample slides 8, which has at least one storage locations 6 and is accessible to the transport device 3 during the operation of the laser scanner 1, and a test part 9 for test slides 10. In this laser scanner according to the invention, the test part 9 is separate from the sample part 7 and is implemented as a test part magazine 9', which is fixedly connected to the laser scanner 1, for one or more test slides 10.

A test slide 10 stored in the test part 9 is thus not manually accessible to an operator in the operating state of the laser scanner 1. This has the advantage that a suitable test slide can be provided at any time, without such a test slide 10 being contaminated or even damaged by improper manipulations by operators. The test part magazine 9' shown here comprises an open insertion side 15.

In the embodiment shown here, the sample part 7 is situated axially above the test part 9 and the test part 9 of the storage unit 4 is fixedly connected to a positioning plate 11 of the storage unit 4, which is movable relative to the sample table 2 of the laser scanner 1. The positioning plate 11 of the storage unit 4 is displaceable essentially perpendicularly relative to the sample plane 49 of the sample table 2. An arbitrary slide 8, 10 can thus be brought to the level of the sample plane 49 defined by the sample table 2 and provided for linear transport onto the sample table 2.

It is preferable for the sample plane 49 of the sample table 2 to be situated essentially horizontally, the sample table 2 carrying a slide 8, 10 above it. However, the sample table 2 can also be situated overhead, so that the inserted slide 8, 10 is situated below the sample table. Any arbitrary other attitude of the sample plane 49 in space is also fundamentally conceivable, but less preferable.

The laser scanner 1, according to the first embodiment shown in FIG. 1, preferably comprises a housing 5, the sample part 7 being implemented as a magazine 7' for a plurality of sample slides 8, which is insertable from the outside into the housing 5 of the laser scanner 1. The sample part 7 is preferably reversibly mountable on the positioning plate 11 of the storage unit 4. In the embodiment shown, a pluggable dovetail connection connects the sample part magazine 7' to the positioning plate 11, which is vertically movable here. The sample part magazine 7' can thus be held on the handle 42 and lowered in the essentially vertical direction into the housing 5 and plugged onto the dovetail 43 of the positioning plate 11. Because the two magazines 7', 9' are situated vertically one above another here, the test part magazine 9', which is screwed fixedly to the positioning plate 11, preferably represents the lower stop for the sample part magazine 7' inserted into the dovetail 43.

The storage locations 6 in the sample part magazine 7' and/or in the test part magazine 9' are implemented to receive slides, which essentially have the dimensions of a standard slide for light microscopy. These storage locations 6 are preferably separated from one another by storage webs 12, so that these slides each rest on two storage webs 12 extending essentially over the entire length of the slides 8, 10.

The sample table 2, shown in a vertical section in FIG. 1, is implemented, for the transfer of sample slides 8 or test slides 10, as movable directly in front of a storage unit 4 for such slides 8, 10 using a spindle drive 84 situated on a suspension 83. The receptacle 34 of the sample table 2 preferably comprises two diametrically opposite grooves 35 for receiving the two longitudinal edges 14 of a sample slide 8 or a test slide 10. The sample plane 49 is preferably situated essentially horizontally. The sample table 2 comprises two fixed webs 36 and a spring-loaded jaw 37, which is movable against these webs 36, having two upright side walls 38, which define the opening width of the grooves 35 together with the lower edges of the webs 36, for the clamped fixing of a slide 8, 10 in the essentially perpendicular direction to the surface of the slide (cf. also FIG. 4).

A controller 40 preferably monitors and/or regulates a motor 87, which drives the spindle drive 84. The controller 40 thus controls the movements of the sample table 2.

Figure 2:
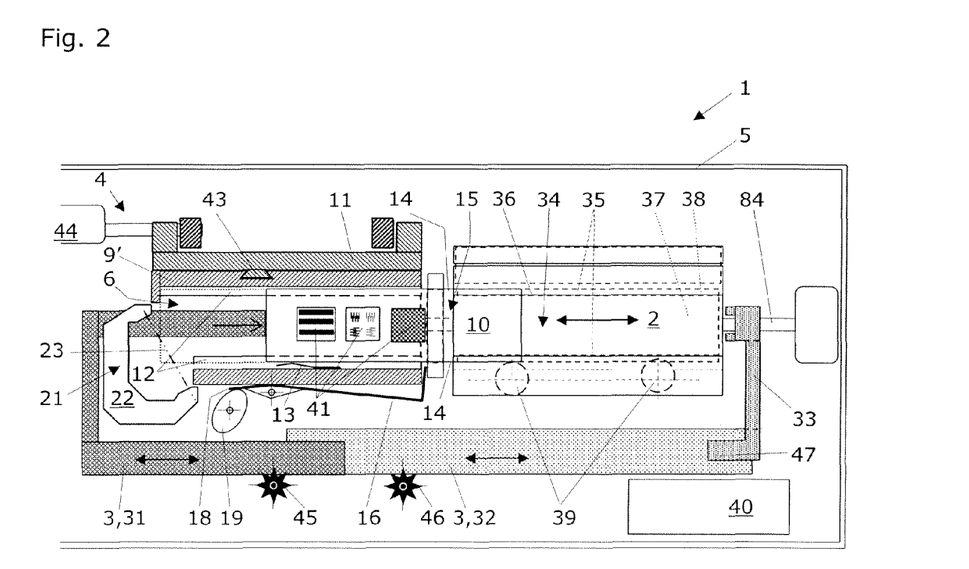
FIG. 2 shows a horizontal partial section through the slide magazines and a top view of the object table placed in front of them upon transfer of a test slide from the test object magazine onto the object table.

FIG. 2 shows a horizontal partial section through the slide magazines shown in FIG. 1 and a top view of the object table placed in front of them upon transfer of a test slide from the test object magazine onto the object table. The test part magazine 9' shown here comprises an open insertion side 15, which can be covered in at least partially its width by an individual foldaway flap 16 extending essentially over the entire stack height of the magazine 9'. This flap 16 is folded away here, so that the test slide shown can be pushed out of the insertion side 15 of the test part magazine 9', without being obstructed by the foldaway flap 16.

In order that the slides 8, 10 are seated essentially without play in the magazines 7', 9', each of these storage locations 6 preferably comprises a contact pressure spring 13, which is elastically applied to a longitudinal edge 14 of an inserted slide. In addition, the particular opposing longitudinal edge 14 of the slide 8, 10 is held in a location defined by the corresponding magazine 7', 9' by the spring pressure, the location being capable of defining a reference for the origin of a coordinate system. Similarly, the sample table 2 is preferably equipped with movable contact pressure parts 39 in the form of rollers (cf. FIG. 2), which also hold the same longitudinal edge 14 in a defined location, whereby a reference for the origin of the coordinate system is again provided.

At least the sample part magazine 7' preferably comprises a monitoring opening 21 extending essentially over the entire stack height on a corner opposite to the insertion side 15 for establishing the presence or absence of a slide in a specific storage location 6. The presence or absence of a slide 8, 10 in a specific storage location 6 can be established using various methods and devices. Thus, for example (cf. FIG. 2), an essentially horizontally propagating light beam 23 or a light barrier of a monitoring device 22 can be oriented diagonally through the magazines 7', 9', if the monitoring opening 21 is transparent to this light beam 23. The deflection, scattering, or attenuation of the light beam 23 by a slide 8, 10 present in a storage space 6 can be easily established using a light-sensitive sensor. While a monitoring opening 21 in the form of a "cut-off corner" is shown in FIG. 2, the light beam 23 can also be sent through the insertion side 15 into the magazine 7', 9' and can hit a sensor on the opposite side, which is not cut off; a diagonal orientation relative to the transport direction of the slides 8, 10 and/or the attachment of a deflection mirror (neither shown) also allows detection of the slides in their magazines even with the sample table 2 close by.

The transport device 3 of the laser scanner 1 preferably comprises an unloading slider 31, which is implemented to engage through the side opposite to the insertion side 15 of the magazines 7', 9' essentially parallel to the sample plane 49 and to transport a sample slide 8 or a test slide 10 from its storage location 6 and out of the insertion side 15 to the sample table 2. This transport device 3 preferably also comprises a loading slider 32, which is implemented to transport a sample slide 8 or a test slide 10 from the sample table 2 and through the insertion side 15 to a storage location 6 in one of the magazines 7', 9'. It is particularly preferable for loading slider 32 to comprise a pivotable flap 33, which can be pivoted up and thus moved away over the slides 8, 10 inserted into the sample table 2, without this flap 33, which is pivotable around an axis 47, touching the slides. This flap can thus be moved over the slides 8, 10 and lowered behind them, upon which the slide can be grasped by the flap 33 and drawn out of the sample table 2. Pivoting up the flap 33 allows the movement of the sample table 2 and the slide 8, 10 inserted therein to the location of the scanner apparatus 72. This pivoting up of the flap 33 around the tilt axis 47 thus allows the free movement of the sample table 2, without the flap 33 being able to come into contact with the inserted slide 8, 10.

The drive 44 for the movable positioning plate 11, the drive 45 for the unloading slider 31, and the drive 46 for the loading slider 32 are preferably each electric motors, which are controlled and monitored by the controller 40.

The sample table 2 shown in FIG. 2 comprises movable contact pressure parts 39, which delimit the opening width of the receptacle 34 using springs, for the clamped fixing of a slide 8, 10 in the direction essentially parallel to the surface of the slide against at least one of the longitudinal edges 14 of the slide. The contact pressure parts 39, which are movable against at least one of the longitudinal edges 14 of the slide, are preferably implemented as rollers each having an essentially vertical axis.

A controller 40 preferably monitors and/or regulates a motor 87, which drives the spindle drive 84. The controller 40 thus monitors the movements of the sample table 2.

Figure 3A:
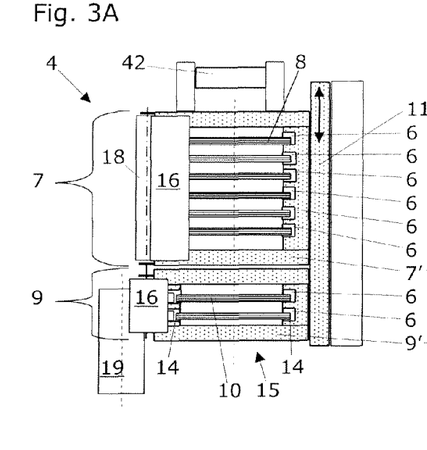

FIG. 3 shows vertical views of the slide magazines having open test object magazine. FIG. 3A shows the insertion side of the two slide magazines in a frontal view seen from the object table. The vertically movable positioning plate 11 is visible on the right side and its mobility is marked by a double arrow. The sample part 7 is situated linearly over the test part 9, the sample part magazine 7', having eight sample slides 8 resting in the storage locations 6 here, being fastened axially above the test part magazine 9' having two test slides 10 here. The foldaway flap 16 of the sample part magazine 7' is closed, while the foldaway flap 16 of the test part magazine 9' is open and essentially exposes the entire width of the insertion side of the test part magazine 9'. The foldaway flap 16 of the test part magazine 9' is folded away here by the eccentric roller 19, which presses on the angled plate 18 of this flap. The eccentric roller 19 is preferably situated at least close to the sample plane 49 defined by the sample table 2, so that in spite of the displacement of the storage unit 4 in height, the correct flap 16 is always folded away. The contact pressure springs of the test part magazine 9' can be seen well, as they press like springs on one side edge 14 of the test slides 10.

Figure 3B:
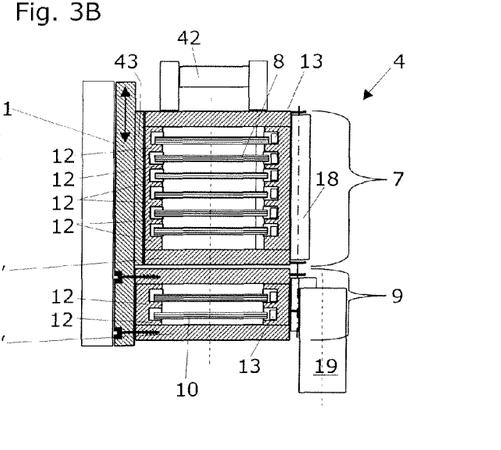

FIG. 3B shows the same two slide magazines in vertical section looking toward the object table. The vertically movable positioning plate 11 is visible on the left side and its mobility is marked by a double arrow. The sample part magazine 7' is pushed over the dovetail 43 of the positioning plate 11 and is held here by the test part magazine 9' in a constant position on the positioning plate 11. The test part magazine 9' is fixedly screwed to the positioning plate 11 here. The contact pressure springs 13 of the sample part magazine 7' and the test part magazine 9' are well visible on the right side of the slide stack here.

FIG. 4 shows vertical partial sections through the object table 2 and its transverse inclination device and/or the tilting mechanism 79, which comprises a motor-driven eccentric 80 and a one-sided rotational axis 81. This tilting mechanism 79 is used for orienting a sample and/or a slide 8, 10 relative to a focal line 101, which runs in a scanning plane 76 (cf. FIG. 5). The focus of the first objective 57 and the movement direction 75 of the scanner head 50 of the laser scanner 1 defined as focal line 101. This focal line 101 itself defines, together with the optical deflection element 56 of the scanner head 50, the scanning plane 76. This scanning plane 76 is thus defined by the movement direction 75 of the scanner head 50 and its optical deflection element 56. This scanning plane 76 is essentially perpendicular to the sample plane 49. This focal line 101 is defined by the movement direction 75 of the scanner head 50 and the focal point 65 of the scanner objective 57 and lies in the sample plane 49 in the correctly adjusted state of the scanner. The rotational axis 81 can be implemented as an actual axis (not shown). However, a virtual rotational axis 81 is preferred, which is formed by a steel spring 104. This steel spring 104 is preferably screwed onto the sample table 2 or onto the support part 103 using a yoke 105. This steel spring 104 causes a counter force to the eccentric 80, so that a simple tilting mechanism without play is provided for the support part 103 of the sample table 2.

Figure 4A:
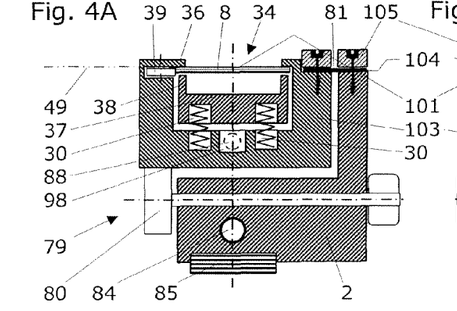
FIG. 4A showing the object table looking toward the slide magazines and having a slide held twice in the closed object table, and FIG. 4B showing the object table looking away from the slide magazines, with open object table, after the removal or before the insertion of a slide.

FIG. 4A shows the object table 2 of the laser scanner 1 looking toward the slide magazines 7', 9' and having a slide 8 held twice in the closed object table 2. The sample table 2 comprises a tilting mechanism 79 having a motorized eccentric 80 and a one-sided rotational axis 81, a slide 8, 10 or a sample being able to be oriented relative to a focal line 101 using this tilting mechanism 79. This focal line 101 preferably lies in the sample plane 49 and in a scanning plane 76, which the scanner head 50 defines using its optical deflection element 56 and its movement direction 75. The scanning plane 76 is preferably perpendicular to the sample plane 49 (cf. also FIG. 5). The transverse inclination of the slide 8, 10 and/or the sample table 2 can be corrected using the eccentric 80, which is preferably motor-driven, so that the focal line 101 of the scanner apparatus 72 comes to rest exactly in the sample plane 49.

The sample plane 49 is preferably situated essentially horizontally. The receptacle 34 of the sample table 2 comprises two diametrically opposite grooves 35 (cf. FIG. 4B) for receiving the two longitudinal edges 14 of the sample slide 8 shown or a test slide 10 (not shown).

For the clamped fixing of a slide 8, 10 in the direction essentially perpendicular to the surface of the slide, the sample table 2 preferably comprises a support part 103 having two fixed webs 36. In addition, the sample table 2 comprises a spring-loaded jaw 37, which is movable against these webs 36, having two upright side walls 38. Together with the lower edges of the webs 36, these side walls 38 define the opening width of the grooves 35. The movable jaw 37 is supported elastically relative to the support part 103 of the sample table 2 using springs 30, so that these springs 30 press the two upright side walls 38 of the movable jaw 37 in a springy manner against the bottom side of the slide 8. A sample slide or a test slide 10, which preferably has at least approximately the dimensions of a glass slide for light microscopy, is thus held clamped in a vertical direction in the sample table 2.

For the clamped fixing of a slide 8, 10 in the direction essentially parallel to the surface of the slide, the sample table 2 comprises contact pressure parts 39 movable against at least one of the longitudinal edges 14 of the slide 8, which delimit the opening width of the receptacle 34 in a springy manner. These contact pressure parts 39, which are movable against at least one of the longitudinal edges 14 of the slide 8, are preferably implemented as rollers each having an essentially vertical axis. The grooves 35 opposite to the rollers 39 define a stop of the sample slide 8 or test slide 10, which is capable of defining the axis of a coordinate system of the laser scanner 1. In addition, a lowering pin 88 is shown plunging into an opening 98 here, which penetrates into the sample table upon the approach of the sample table 2 and the storage unit 4 and draws the jaw 37 and the side walls 38 away from the webs 36 of the support part 103 using this penetration.

Figure 4B:
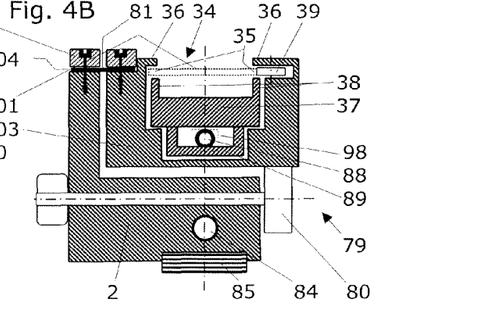

FIG. 4B shows the object table 2 looking away from the slide magazines 7', 9', with open object table 2, after the removal and/or before the insertion of a slide 8, 10. Because a slide 8, 10 is not currently located in the sample table 2, the roller-shaped contact pressure parts 39 are in their extreme position. The roller-shaped contact pressure parts 39 are displaced from this extreme position against the pressure of spring elements as soon as a slide 8, 10 is inserted into the sample table 2. It is also well visible here how the lowering pin 88 runs on a ramp 89, so that the movable jaw 37 of the sample table 2 is pulled down somewhat and the insertion of a slide 8, 10 into the receptacle 34 of the sample table 2 is made possible.

Figure 5:
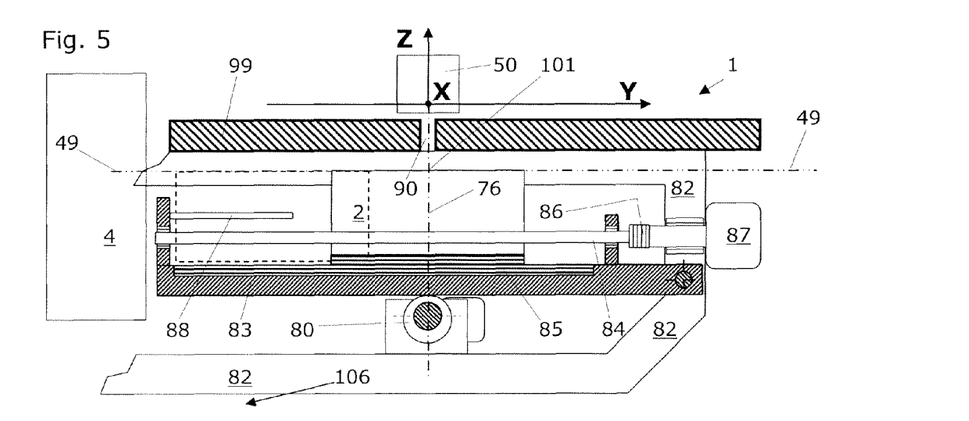
FIG. 5 shows a vertical partial section through the object table and its height adjustment and longitudinal inclination device.

FIG. 5 shows a vertical partial section through the object table and its height adjustment and longitudinal inclination device. The sample plane 49 defined by the sample table 2 is adjustable essentially in the Z direction (in the vertical direction here), in that the sample table 2, which is linearly fastened on a suspension 83 and is linearly displaceable, rests together with this suspension 83 on a motor-driven eccentric 106 and is fastened on one side on a frame 82 so it is pivotable. If the eccentric 106 is rotated somewhat, the suspension 83 rises or sinks correspondingly with the sample table 2. The plane of the sample table 2, i.e., the sample plane 49, can be brought into correspondence with the plane of a storage location 6 in the sample part magazine 7' or in the test part magazine 9' of the storage unit 4 by this movement, so that a linear transfer can be performed between one of these magazines 7', 9' and the sample table. The corresponding magazine is preferably provided in the Z direction by a displacement of the movable positioning plate 11, so that only a possible fine adjustment must be performed using the eccentric 106 of the sample table suspension 83. Using the eccentric 106, which is preferably motor-driven, the longitudinal inclination of the slide 8, 10 and/or the sample table 2 can be corrected, so that the focal line 101 of the scanner apparatus 72 comes to rest exactly in the sample plane 49. A displacement in height, i.e., along a Z axis, also actually occurs with the correction of the longitudinal inclination.

For the purpose of such a slide transfer, the sample table 2 is preferably moved as close as possible to the storage unit 4 in the essentially horizontal Y direction. As the sample table 2 approaches the storage unit 4, a lowering pin 88 penetrates into the sample table 2 and thus lowers a support of the receptacle 34 of the sample table 2 to receive a slide. The sample table 2 is thus provided for receiving a slide 8, 10. This approach is preferably performed using a spindle drive 84 mounted on the suspension 83 and along a linear guide 85. The spindle drive 84 is connected via a flexible coupling 86 to the motor 87, so that exact linear guiding of the sample table 2 essentially in the Y direction can also be performed if the sample plane 49 encloses a small angle of inclination to the horizontal. The goal of the adjustability of the sample table 2 using the eccentric 80 is primarily the orientation of the sample plane 49 to a focal line 101, which is defined by a scanner head 50 of the laser scanner 1 oscillating in the X direction (perpendicular to the plane of the drawing here). This scanner head 50 moves very rapidly in the X direction and on the top of a partition plate 99. This partition plate has a scanning opening 90. The scanner head 50 is preferably lowered into this scanning opening 90, so that the light beams emitted therefrom are incident on the sample at small intervals, and the scanner head 50 can absorb the fluorescence emissions coming from the sample as effectively as possible and relay them to one detector 61 or to multiple detectors 61, 61'.

Figure 6:
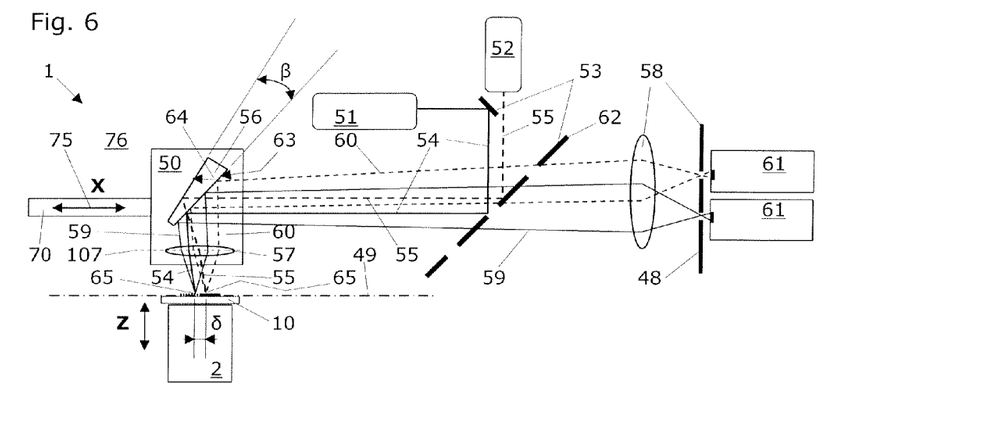
FIG. 6 shows a schematic sketch having essential optical elements of the laser scanner having a scanner head according to a first embodiment.

FIG. 6 shows a schematic sketch having essential optical elements of the laser scanner 1 having a scanner head 50 according to a first embodiment. The laser scanner 1 for imaging and/or measuring fluorescent samples, which are located on slides and are treated using two different fluorescent pigments, comprises a sample table 2 movable by a motor having a receptacle for a sample slide 10 in a sample plate 49. A first laser 51 and a second laser 52 and a first optical system 53 provide two laser beams 54, 55 of different wavelengths, which are oriented parallel to one another and run parallel to this plane 49. A scanner apparatus 72 comprises a scanner head 50, which is movable back and forth parallel to this plane 49, having an optical deflection element 56 for deflecting the laser beams 54, 55 toward the sample. A first objective 57 focuses the laser beams 54, 55 on the sample in the plane 49. This first objective 57 has a main plane 107, which is preferably situated parallel to the sample plane 49.

A second optical system 58 conducts the emission beam bundles 59, 60, which are triggered by the laser beams 54, 55 on the sample and conducted by the first objective 57 and the deflection element 56 in a direction essentially parallel to the plane 49, to the detectors 61, 61'. Two such detectors 61, 61' acquire the emission beam bundles 59, 60 of different wavelengths, which originate from the samples. The openings of the apertures 48 preferably have a larger diameter than the focused emission beam bundles 59, 60; however, they may also essentially correspond to the dimensions of the focused emission beam bundles 59, 60, whereby a confocal laser scanner 1 would be provided.

The optical deflection element 56 of the laser scanner 1 according to the invention comprises a wedge-shaped dichroic mirror 62 having front and rear dichroic surfaces 63, 64, which are situated at an intermediate angle β to one another. The wedge-shaped dichroic mirror 62 is set so that the two laser beams 54, 55 are each reflected on one of the surfaces 63, 64. The wedge-shaped dichroic mirror 62 causes a spatial separation of the two resulting focal points 65 and the two emission beam bundles 59, 60, which are conducted in the direction of the detector 61, 61', by the intermediate angle β. The two resulting focal points 65, 65' are situated at a distance δ to one another in the sample plane 49. In this first embodiment shown in FIG. 6, the optical deflection element 56 is a wedge-shaped dichroic mirror 62. The rear dichroic surface 64 of the wedge-shaped dichroic mirror 62 is preferably implemented for reflecting a first laser beam 54 and its front dichroic surface 63 for reflecting a second laser beam 55 and the two emission beam bundles 59, 60.

The second optical system 58 comprises elements known per se such as a second objective 57', which focuses the incoming emission beam bundles 59, 60 in one point each. The second optical system 58 additionally comprises an aperture 48, whose openings are preferably significantly larger than the focused emission beam bundles 59, 60, which pass through these openings. According to a particularly preferred embodiment, the laser scanner 1 is thus based on a non-confocal imaging principle. These focused emission beam bundles 59, 60 are then each incident on one detector 61, 61', which measures the intensity of the particular emission beam bundle 59,60. This second objective 57' can be implemented as achromatic or as a simple lens.

Figure 7A:
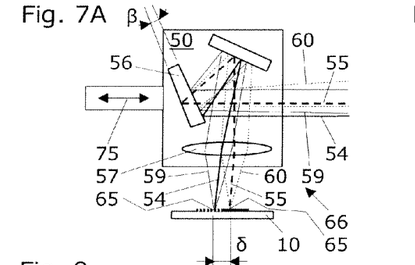
FIG. 7A showing a second embodiment of the scanner head.

FIG. 7 shows schematic sketches of the scanner head of the laser scanner according to the invention. FIG. 7A shows a second embodiment of the scanner head 50, in which the optical deflection element 56 is implemented as a pentamirror configuration 66 having a wedge-shaped dichroic mirror 62 and a single mirror 67. As already described in the first embodiment (cf. FIG. 6), the rear dichroic surface 64 of the wedge-shaped dichroic mirror 62 is implemented for reflecting a first laser beam 54 and its front dichroic surface 63 is implemented for reflecting a second laser beam 55 and the two emission beam bundles 59, 60.

Figure 7B:
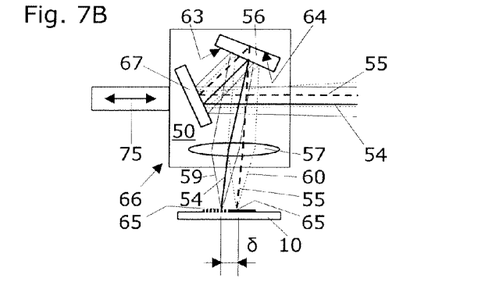
FIG. 7B showing a third embodiment of the scanner head.

FIG. 7B shows a third embodiment of the scanner head 50, in which the optical deflection element 56 is also implemented as a pentamirror configuration 66 having a wedge-shaped dichroic mirror 62 and a single mirror 67. In contrast to the second embodiment (cf. FIG. 7A), the configuration of the dichroic mirror 62 and the single mirror 67 is exchanged. The rear dichroic surface 64 of the wedge-shaped dichroic mirror 62 is implemented for reflecting a first laser beam 54 and its front dichroic surface 63 is implemented for reflecting a second laser beam 55 and the first and second emission beam bundles 59, 60.

It is obvious that the embodiments just described and further combinations may be exchanged arbitrarily. However, the first embodiment according to FIG. 6, in which the optical deflection element 56 is implemented as a wedge-shaped dichroic mirror 62 or the second implementation according to FIG. 7A, in which the optical deflection element 56 is implemented as a pentamirror configuration 66 having a wedge-shaped dichroic mirror 62 and a single mirror 67, is preferred. For all pentamirror configurations 66, the front surface 63 and the single mirror 67 preferably enclose an angle of 22.5°.

Figure 8:
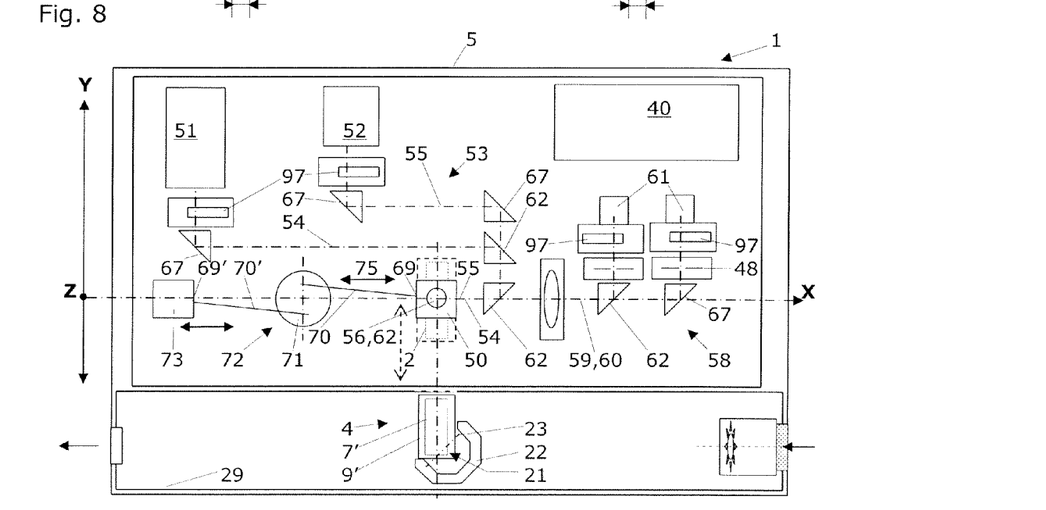
FIG. 8 shows a horizontal partial section through a laser scanner having essential optical elements, a scanner apparatus having scanner head, and an object table having slide magazines.

FIG. 8 shows a horizontal partial section through a laser scanner 1 having essential optical elements of a first optical system 53 for providing excitation light and a second optical system 58 for acquiring the triggered fluorescence emissions of the samples, a scanner apparatus 72 having scanner head 50 and an object table 2 having a storage unit 4 comprising slide magazines 7', 9'. All essential optical elements and the scanner apparatus 72 are preferably situated on a shared partition plate 99 and the sample table 2 is situated below this partition plate 99 (cf. FIG. 5).

Essential optical elements of the first optical system 53 are situated in a housing 5 and comprise at least a first laser 51 and optionally a second laser 52, filter wheels 97 for the laser beams 54, 55 originating from the laser or lasers 51, 52 and a number of dichroic mirrors 62 and single mirrors 67 for deflecting the laser beams 54, 55 from the lasers 51, 52 in a direction parallel to the X direction.

The essential optical elements of the second optical system 58 are situated in the same housing 5 and comprise one or more detectors 61, 61', these upstream filter wheels 97, and apertures 48 for the emission beam bundles 59, 60 originating from the samples, as well as a number of dichroic mirrors 62 and single mirrors 67 for deflecting the emission beam bundles 59, 60 from a direction parallel to the X direction in the direction of the detectors 61, 61'.

The scanner apparatus 72 comprises a drive 71, the scanner head 50, and preferably a counter oscillator 73 having a mass equal or at least equivalent to the scanner head 50 for impulse compensation. Scanner head and counter oscillator are connected to the drive 71 using connecting rods 70, 70' and are each fastened to a precise linear guide (not shown). The scanner head 50 is caused to move rapidly back and forth in the movement direction 75 (cf. solid double arrows), which simultaneously defines the scanning axis 75, by the drive 71. The counter oscillator 73 always executes an opposing movement, whereby the partition plate 99 and thus the entire laser scanner 1 are kept calm in spite of the preferred high scanning speed of the scanner head 50. The scanning axis 75 is parallel to the X axis or is particularly coincident thereto. The scanner head 50 comprises an optical deflection element 56, which is implemented as a dichroic mirror 62, for example. This deflection element 56 can be implemented as a full mirror, prism, pentaprism, pentamirror configuration, or as a combination of the elements listed here. This deflection element 56 conducts the laser beams 54, 55 of the first optical system 53 onto the samples on the sample table 2, on the one hand, and the emission beam bundles 59, 60 emitted by the samples in the direction of the second optical system 58, on the other hand.

The movement direction of the sample table 2 situated below the partition plate 99 runs in the direction of the Y axis perpendicular to the X axis and the scanning axis 75. The storage unit 4 having the sample slides 8 stored in the sample part magazine 7' and the test slides 10 stored in a test part magazine 9' is preferably situated in an area outside the partition plate 99. The presence of a slide 8, 10 in a specific storage location 6 of these magazines 7', 9' is preferably checked using a monitoring device 22. This monitoring device preferably comprises a light beam 23, which penetrates a monitoring opening 21 for these monitoring purposes.

It is particularly preferable for a service technician to insert one or more test slides 10 individually into a sample part magazine 7' and to insert this sample part magazine 7' properly into the laser scanner 1. Correspondingly programmed firmware in the controller 40 of the laser scanner 1 is then preferably activated by inputting a personal identification number (PIN) of the service technician and/or by inputting a code for service technicians. The firmware thus activated makes the controller 40 of the laser scanner 1 capable of controlling the automatic transport of each of these test slides 10 from the sample part magazine 7' to the sample table 2 and further into a storage location 6 of the test part magazine 9'. According to this particularly preferred embodiment, any manual engagement in the test part magazine 9' is made impossible. A service technician can only retrieve the test slides 10, which are preferably enclosed in the additional housing 29, using suitable tools in special emergency cases. The controller 40 of the laser scanner 1 according to the invention is preferably implemented for controlling an automated internal instrument check which is executed on the basis of test slides 10.

The sample table 2 is preferably implemented as motor-driven to be moved up to directly in front of the storage unit 4 and its location and movement are monitored by the controller 40. This is also true for the positioning plate 11 of the storage unit 4 for selecting the slide 8, 10 to be studied and for the rotatable eccentric roller 19 for folding away the flap 16. In addition, it is preferable for the unloading slider 31 for transporting a slide 8, 10 to the sample table 2 to be implemented as motorized for the automated selection and provision of a sample slide 8 or test slide 10 on the sample table 2 and its location and movement to be monitored by the controller 40. This is also true for the loading slider 32 for transporting a slide 8, 10 to the storage unit 4 when the slide is put back into a storage location 6 of the sample part magazine 7' or the test part magazine 9'.

Figure 9:
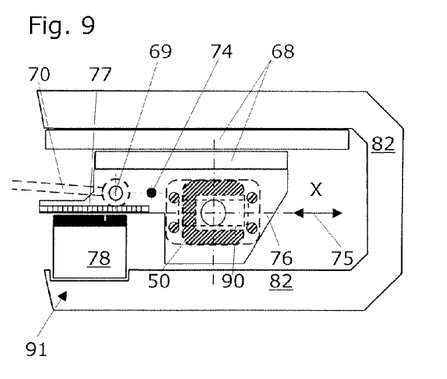
FIG. 9 shows a horizontal partial section through the scanner head of the laser scanner having the associated position encoder.

FIG. 9 shows a horizontal partial section through the scanner head 50 of the laser scanner 1 having the associated position encoder 91. A linear guide 68 is fastened on a frame 82, on which the scanner head 50 is situated so it is movable in the X direction and plunges into a scanning opening 90. In this case, the X axis is coincident with the movement direction 75 of the scanner head 50, this movement direction 75 defining a scanning plane 76 together with first and second laser beams 54, 55, which are deflected toward the sample (not shown) situated below the scanner head 50. This scanning plane 76 is preferably perpendicular to the sample plane 49. The scanner head 50 comprises a scale 77, which is situated at a distance to a fixed linear measuring system 78 of the laser scanner 1 and in this scanning plane 76. The sample table 2 is preferably implemented as linearly movable in a Y direction of a Cartesian coordinate system situated perpendicularly to the X axis 75 and as motor-driven.

The scanner head having all of its optical elements, fasteners, the scale 77, and a part of the linear guide has a mass center of gravity 74. This mass center of gravity 74 is situated in the movement direction 75 of the scanner head 50 on a line with a connecting rod attachment point 69, which connects the connecting rod 70 of the scanner head 50 to the drive 71. This connecting rod attachment point 69 can be implemented as an axis, for example; however, it is preferable to implement the connecting rod attachment point as a flexural pivot.

Figure 10:
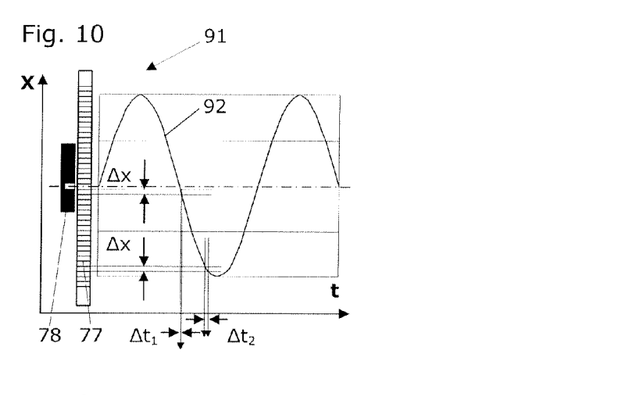
FIG. 10 shows a schematic sketch of the position encoder for the scanner head and its nonlinear movement during scanning as an X/t diagram, which indicates the different time durations ($\Delta t_1$; $\Delta t_2$) for the acquisition of the fluorescent light originating from an object depending on the position of a number of pixels ($\Delta x$) on the X axis.

FIG. 10 shows a schematic sketch of a position encoder 91 for the scanner head 50 and its nonlinear movement when scanning as an X/t diagram. This X/t diagram indicates the different time durations ($\Delta t_1$; $\Delta t_2$) for the acquisition of a pixel ($\Delta x$) depending on the position on the X axis. The position encoder signal 92 approximately corresponds to a sine curve, which has its maxima at the extreme points (endpoints) of a scanning line of the laser had 50. Because of the reversal of the scanning direction at these endpoints and the movement, which is thus slowed, the scanner head requires a longer time ($\Delta t_2$) for the same section ($\Delta x$) than at the achievable highest speed of the scanner head in a middle position between the turning points, in which it passes through the same section ($\Delta x$) in a much shorter time ($\Delta t_2$). The pixel ($\Delta x$) and the corresponding location and moment are correlated with one another and associated with the intensity measured at this moment. The sum of all measured pixels results in a two-dimensional image. The correlation of the location of these pixels in the sample plane 49 to the intensity of the fluorescence intensity measured at this location finally determines the resolution of the laser scanner 1 in combination with the pixel size.

FIGS. 11 through 15 show diagrams of proposed solutions, in which the signal integration (I) is shown as a function of time (t).

Figure 11:
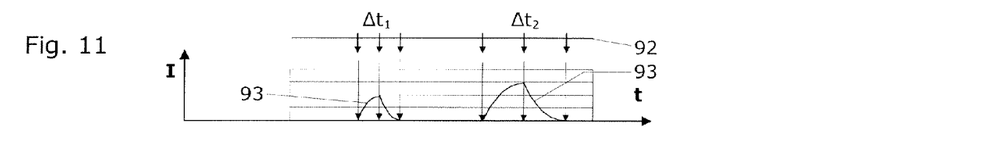
FIG. 11 showing a first proposed solution, in which the position encoder triggers the data acquisition using a passive integrator.

FIG. 11 shows a first proposed solution, in which the position encoder triggers the data acquisition using a passive integrator (RC element). This proposed solution for improving the sensitivity of the laser scanner still contains some possible disadvantages, however. Thus, the measured intensity is higher at the edge of the scanning area, because integration is performed longer per pixel here. In addition, the resolution of the laser scanner is reduced because of the decay characteristic of the RC element.

Figure 12:
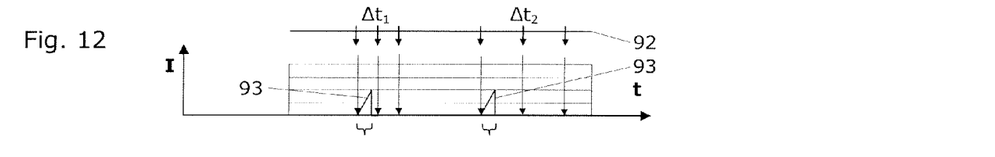
FIG. 12 showing a second proposed solution, in which the position encoder triggers the data acquisition using a switchable integrator at constant integration time.

FIG. 12 shows a second proposed solution, in which the position encoder triggers the data acquisition using a switchable integrator at constant integration time. This proposed solution for improving the sensitivity of the laser scanner still contains some unacceptable disadvantages, however. Thus, the erasing time for the integrator reduces the sensitivity, because this time is not available for the signal acquisition. This erasing time occupies a significant proportion of the measuring time in particular at small resolutions, i.e., very small "pixel times" (pixel dwell times). Moreover, additional noise is generated by the erasing procedure. In addition, so-called "undersampling" results at the edge of the scanning area. Unequal conditions of the data acquisition (shorter or longer intervals between two trigger impulses) may also result in inhomogeneities between central and edge areas.

Figure 13:
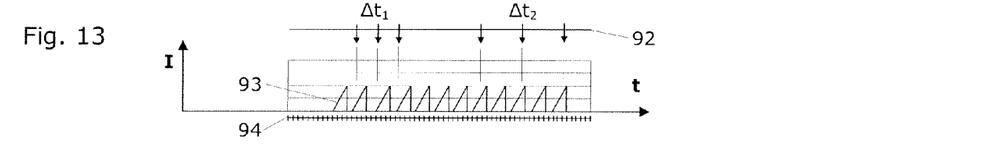
FIG. 13 showing a third proposed solution, in which the position encoder signal is chronologically acquired as an event and each signal is associated with the moment of its occurrence via a timebase, the signal integration being triggered in continuous progression by the timebase.

FIG. 13 shows a third proposed solution, in which the position encoder signal is chronologically acquired as an event and each signal is associated via a timebase with the moment of its occurrence, the signal integration being triggered in continuous progression by the timebase. The advantage in relation to the second proposed solution for improving the sensitivity of the laser scanner, according to which identical "electronic conditions" now prevail over the entire scanning area, is opposed by the disadvantages known from the second proposed solution. These disadvantages result in that the additional noise is generated by the erasing procedure and the erasing time reduces the sensitivity.

Figure 14:
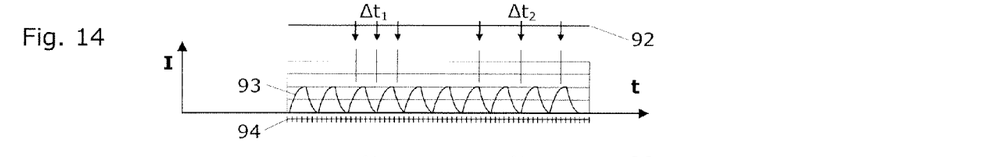
FIG. 14 showing a fourth proposed solution corresponding to the third proposed solution, a passive RC element being used for integration, however.

FIG. 14 shows a fourth proposed solution corresponding to the third proposed solution, a passive RC element being used for integration, however. The advantage in relation to the third proposed solution for improving the sensitivity of the laser scanner is that here no losses in the sensitivity must still be accepted, because the erasing time and the additional noise due to the erasing procedure are dispensed with. In contrast, the clear disadvantage because of the reduced resolution caused by the decay characteristic of the RC element still exists. It is noted here that the reduction of the time constant of the RC element would solve the resolution problems; however, this would cause losses in the sensitivity. The time constant of the RC element must be at least in the order of magnitude of one pixel, but is preferably in the order of magnitude of one data acquisition interval, because otherwise short signals (typically of single photons) would possibly be overlooked, i.e., not detected. The time between two conversion points of the A/D converter is referred to as a data acquisition interval.

Figure 15:
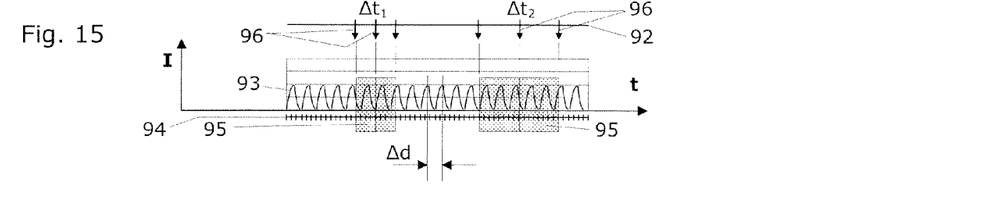
FIG. 15 showing a fifth proposed solution which corresponds to the fourth proposed solution, multiple measurements being executed per pixel, however.

FIG. 15 shows a fifth proposed solution, which corresponds to the fourth proposed solution, but with several measurements being performed per pixel. The intensity of a pixel is preferably calculated as a mean value of all data points which lie inside the time marks for this pixel (and possibly refined still further by interpolation). The last still existing disadvantage relative to the fourth proposal is eliminated here, because reduced resolution no longer results due to the lower decay time of the RC element.

The findings from the various proposed solutions shown result in preferred embodiments of the data acquisition method according to the invention:

Every detector signal (93) generated by a detector (61) is preferably integrated by an integrator of the controller (40), the moment of the corresponding position encoder signal (92) being associated with each part of an integrated detector signal (93) via the timebase (94), and each signal integration being triggered in continuous progression by the timebase (94) and being performed by the controller (40) at constant integration time.

It is particularly preferable for the signal integration to be executed using a passive RC element, the time constant selected for the RC element lying at least in the order of magnitude of one data acquisition interval Δd. A data acquisition interval is one continuous acquisition of the integrated detector signals 93 between two detector signal maxima, which is constant in time (cf. Δd in FIG. 15).

It is especially preferable for the intensity of a pixel 95 to be calculated as a mean value of all data points which lie within time marks 96 for this pixel 95. For further refinement, an interpolation method can also be used, which considers data acquisition intervals Δd lying incompletely between the time marks of a pixel and proportionally interpolates their associated measured values.

Figure 16:
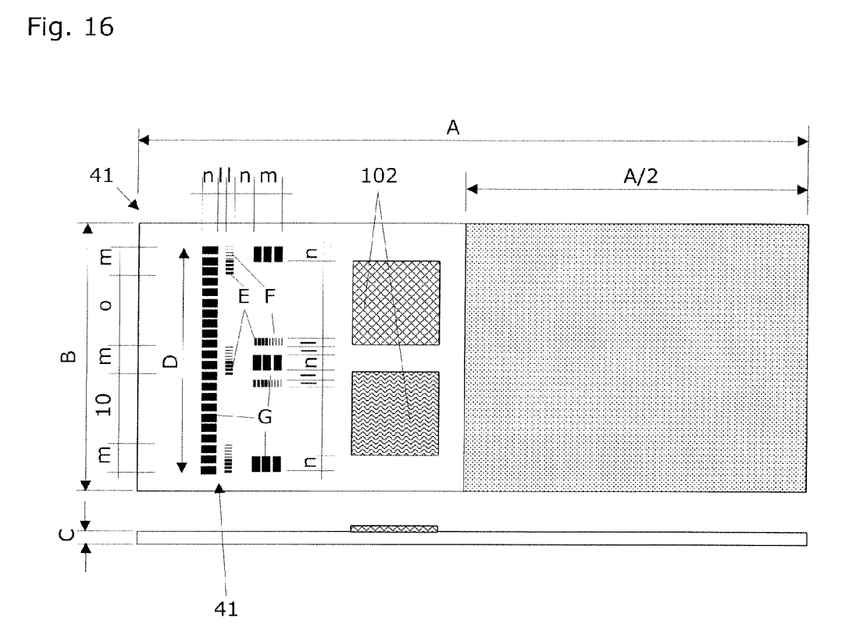
FIG. 16 is a schematic illustration of a test slide which has the format of a standard slide for light microscope and exclusively comprising essentially light-stable test structures.

FIG. 16 shows a preferred test slide 10, which has the format of a standard slide for light microscopy and exclusively comprises essentially light-stable test structures 41. A test structure is referred to as "essentially light-stable" if it does not suffer measurable damage during normal usage, i.e., in the event of the radiation load typically occurring during test methods. The radiation of a test slide 10 with a laser beams 54, 55 for minutes or even hours and/or leaving a test slide 10 in an unprotected location for a long time (for example, exposed to ambient light) are not referred to as "normal use".

Following Table 1 gives an overview of the most typical glass slides for light microscopy:

| Type | Inches: 1 × 3 inches | Metric: 25 × 75 mm |
|---|---|---|
| | Dimensions: | |
| Length × width (Tolerances) | 76.2 mm × 25.4 mm (±0.5 mm) | 76 mm × 25 mm (±0.5 mm) |
| | Thickness: | |
| "Standard" | 1.02 mm (±0.05 mm) | 1.02 mm (±0.05 mm) |
| "Thick" | 1.2 mm (±0.1 mm) | |
| | Treatment: | |
| Corners | Sharp, beveled | Sharp, beveled |
| Edges | Sharp, beveled | Sharp, beveled |
| Surfaces | Blank, sandblasted, on one or both sides | Blank, sandblasted on one or both sides |

The exemplary test slide 10 shown in FIG. 16 has a surface having a length A of 75 mm, a width B of 25 mm, and a thickness C of 1 mm. One half of the surface A/2 is matted (for example, using grinding). The other half has a preferred line pattern having a width D of 20 mm.

This line pattern preferably comprises a vapor-deposited chromium layer produced using a mask. The capital letters E, F, G identify a specific number of line pairs per millimeter (lp/mm) and the lowercase letters l, m, n, o identify specific dimensions as follows:

E=50 lp/mm; F=100 lp/mm; G=10 lp/mm;
l=0.5 mm; m=2 mm; n=1 mm; o=7 mm.

All of these structures 41 are preferably exclusively essentially light-stable and non-fluorescent.

The laser scanner 1 according to the invention is designed for imaging and measuring two-dimensional objects. Correspondingly, a sensitivity calibration must be valid precisely for these "flat" objects. Two-dimensional fluorescent samples which are both light-stable and also chemically resistant over long periods of time cannot be produced or can only be produced with great difficulty, however.

In contrast, objects which have a three-dimensional extension may be measured. Because the intensities measured on such three-dimensional objects are very strongly dependent on the depth of field of the laser scanner and the particular positioning in the focus (i.e., in the Z direction), such three-dimensional objects are not directly suitable for calibration of signal intensity or sensitivity, however. However, materials 102, such as fluorescent pigments embedded in plastic or doped glasses, which are extensively light-stable and chemically resistant, exist as so-called "bulk material".

The orientation of the sample table 2 and the storage unit of the laser scanner 1 in space is actually arbitrary. This is also true for the scanner apparatus 72, which is balanced well and/or impulse-compensated using counter oscillator 73. The sample plane 49 of the sample table 2 can also be situated essentially horizontally but suspended overhead. However, an upright configuration of the sample table according to FIGS. 1 and 2 and/or 4 through 7 is preferred.

Identical features or elements of the laser scanner 1 according to the invention are each provided with identical reference numerals, even if these elements are not described in detail in all cases.

The following features are also a component of the data acquisition method according to the invention using a laser scanner 1 for imaging and/or measuring fluorescent samples which are located on slides and treated using fluorescent pigments, according to which:

The sample plane 49 is situated essentially horizontally and the movement direction 75 of the scanner head 50 preferably defines an X axis or scanning axis, the sample table 2 being moved linearly in a Y direction of a Cartesian coordinate system situated perpendicularly thereto. Two laser beams 54, 55 of different wavelengths, which are oriented parallel to one another and run parallel to the sample plane 49, are provided using the at least one laser 51, 52 and the first optical system 53 and are deflected toward the sample using an optical deflection element 56 of a scanner apparatus 72. These laser beams 54, 55 are preferably focused using the first objective 57 on the sample in the plane 49, after which the emission beam bundles 59, 60 of different wavelengths, which are triggered by the laser beams 54, 55 on the sample and are deflected by the first objective 57 and the deflection element 56 in a direction essentially parallel to the plane 49, are conducted using the second optical system 58 to two detectors 61, 61' and acquired by these detectors 61, 61'. The use of a wedge-shaped dichroic mirror 62 having front and rear dichroic surfaces 63, 64 situated at an intermediate angle β to one another as a part of the optical deflection element 56 is particularly preferred. The wedge-shaped dichroic mirror 62 is preferably set so that the two laser beams 54, 55 are each reflected on one of the surfaces 63, 64, so that the wedge-shaped dichroic mirror 62 causes a spatial separation of both resulting focal points 65 and both emission beam bundles 59, 60 deflected in the direction of the detectors 61, 61' through the intermediate angle β.

An optical deflection element 56 implemented as a pentamirror configuration 66 having a wedge-shaped dichroic mirror 62 and a single mirror 67 is used, this pentamirror configuration 66 correcting tilts of the scanner head 50 around a Y axis running perpendicularly to the scanning axis 75 so that the resulting focal points 65 do not change their current position in the sample plane 49.

The deflection of the scanner head 50 in the X axis 75 is measured using a scale 77, which is situated at a distance to a linear measuring system 78 of the laser scanner 1 in this scanning plane 76. Alternatively, it is preferred that the deflection of the scanner head 50 in the X axis 75 is measured using a scale 77, which is at least situated in proximity to the main plane 107 of the first objective 57.

It is particularly preferred that the scanner head 50 defines a scanning plane 76, which is perpendicular to the sample plane 49, using its optical deflection element 56 and its movement direction 75, the deflection of the scanner head 50 in the X axis 75 being measured using a scale 77, which is situated at a distance to a linear measuring system 78 of the laser scanner 1 and in this scanning plane 76. This scale 77 is preferably situated in the scanning plane 76 or at least in direct proximity to this scanning plane 76. This scale 77 is preferably also situated in the main plane 107 of the first objective 57 (cf. FIGS. 6 and 7) or at least in direct proximity to this main plane 107.

Instead of a normal scan and/or a normally scanned field in the XY direction and thus parallel to the sample plane 49, a scan is performed in the XZ direction (Z profile), in that a field is scanned which stands at least essentially vertically on the sample plane 49. The directly measured Z profile represents the measured intensity as a function of the Z coordinates (I=I(Z)). In place of this Z profile, the first derivative of the corresponding intensities (dI=dI(z)/dz) is preferably calculated, whereby a two-dimensional intensity distribution is again provided. The maximum of the first derivative is thus a measure of the intensity measured by the laser scanner 1 on the surface of the sample.

The materials 102 suitable for this calibration method may be situated together with the vapor-deposited line patterns on the same test slide 10 or on a separate test slide. These flat, three-dimensional materials 102 preferably have an extension of 2×2 mm to 10×10 mm parallel to the sample plane 49 and have a thickness of approximately 0.1 to 2 mm, preferably a thickness of approximately 1 mm (cf. FIG. 16).

One skilled in the art recognizes the function of a dichroic mirror as an optical element, which is transparent to a part of the wavelength spectrum and reflects another part of this wavelength spectrum. One skilled in the art therefore refers here to a wavelength-selective transmission and reflection. Combinations and/or variants of the described embodiments of the present invention resulting for one skilled in the art from the present description are thus within the scope of the invention.

LIST OF REFERENCE NUMERALS 1 laser scanner
2 sample table
3 transport device
4 storage unit
5 housing
6 storage location
7 sample part
7' sample part magazine
8 sample slide
9 test part
9' test part magazine
10 test slide
11 movable positioning plate
12 storage webs
13 contact pressure spring
14 longitudinal edge of slide
15 insertion side
16 foldaway flap
18 angled plate
19 eccentric roller
21 monitoring opening
22 monitoring device
23 light beam
29 additional housing
30 spring
31 unloading slider
32 loading slider
33 pivotable flap
34 receptacle
35 diametrically opposite grooves
36 fixed webs
37 movable jaw
38 upright side walls
39 movable contact pressure parts
40 controller
41 light-stable test structures
42 handle
43 dovetail
44 drive for 11
45 drive for 31
46 drive for 32
47 tilt axis of 33
48 aperture
49 plane, sample plane
50 scanner head 51 first laser
52 second laser
53 first optical system
54 first laser beam
55 second laser beam
56 optical deflection element
57 first objective
57' second objective
58 second optical system
59 first emission beam bundle
60 second emission beam bundle
61 first detector
61' second detector
62 dichroic mirror
63 front surface
64 rear surface
65 resulting focal points
66 pentamirror configuration
67 single mirror
68 linear guide
69, 69' connecting rod attachment point
70, 70' connecting rod
71 drive
72 scanner apparatus
73 counter oscillator
74 mass center of gravity
75 movement direction X axis, scanning axis
76 scanning plane
77 scale
78 linear measuring system
79 tilt mechanism
80 eccentric, eccentric device
81 rotational axis
82 frame
83 suspension
84 spindle drive
85 linear guide
86 coupling
87 motor
88 lowering pin
89 ramp
90 scanning opening
91 position encoder
92 position encoder signal
93 detector signals
94 timebase
95 pixel
96 time marks
97 filter wheel
98 opening
99 partition plate
101 focal line
102 flat materials
103 support part of 2
104 steel spring
105 yoke
106 eccentric, eccentric device
107 main plane of objective 57

The invention claimed is:

1. A data acquisition method using a laser scanner (1) for the pixel-precise imaging of samples, which are located on slides (8) and treated using fluorescent pigments, this laser scanner (1) comprising:
   (a) a sample table (2) having a receptacle (34) for slides (8) in a sample plane (49);
   (b) at least one laser (51, 52) and a first optical system (53) for providing at least one laser beam (54, 55) for exciting the fluorescent samples;
   (c) a motor-driven scanner head (50), which moves non-linearly in space, having a first optical deflection element (56) for deflecting the laser beams (54, 55) toward the sample and for scanning this sample in at least one movement direction (75);
   (d) a first objective (57) for focusing the laser beams (54, 55) on the sample in the plane (49);
   (e) a second optical system (58) for relaying emission beam bundles (59, 60), which are triggered by the laser beams (54, 55) on the sample and are deflected by the first objective (57) and the deflection element (56), to at least one detector (61);
   (f) a position encoder (91), which emits position encoder signals (92), which indicate the instantaneous whereabouts of the scanner head (50) in relation to a zero point;
   (g) an electronic element for filtering detector signals (93) of the detector (61) using a defined time constant; and
   (h) an A/D converter for digitizing the filtered detector signals (93),
   wherein the scanner head (50) is displaced on a linear guide (68), which defines the movement direction (75) of the scanner head (50),
   wherein the filtered detector signals (93) of the A/D converter and the position encoder signals (92) are acquired chronologically in parallel and continuously but independently of one another by a computer unit and/or a controller (40) and related to a common timebase (94), the A/D conversion being performed with sufficient frequency that more than one data point of the A/D converter is always associated with each pixel (95) of an image,
   and wherein the detector signal (93) generated by a detector (61) is digitized by the A/D converter of this controller (40), the moment of the corresponding position encoder signal (92) being associated with each conversion point of the A/D converter via the timebase (94), and each digitization being triggered in continuous progression by the timebase (94) and being performed by the controller (40) at a constant and equal time for all data acquisition intervals (Δd).

2. The data acquisition method according to claim 1, wherein the signal filtering is executed using a passive RC element, the time constant selected for the RC element being in the order of magnitude of one data acquisition interval (Δd).

3. The data acquisition method according to claim 2, wherein the intensity of the pixel (95) is calculated as the mean value of all data points which lie within time marks (96) for this pixel (95).

4. The data acquisition method according to claim 3, wherein, in addition, the measured values of data acquisition intervals lying incompletely between the time marks of the pixel are proportionally interpolated.

5. The data acquisition method according to claim 1, wherein the signal filtering is executed using a passive RC element, the time constant selected for the RC element being a part of the order of magnitude of one pixel (95).

6. The data acquisition method according to claim 1, wherein a pixel resolution which is 2.0 μm or better is achieved using the laser scanner (1) when imaging fluorescent samples located on slides (8) and treated using fluorescent pigments.

7. The data acquisition method according to claim 6, wherein pixels (95) having a size of 2 μm are imaged with at least two individual detector signals (93) using the laser scanner (1).

8. The data acquisition method according to claim 1, wherein the connecting rod attachment point (69) of the scanner head (50) is situated in the movement direction (75) on a line with a mass center of gravity (74) of the scanner head (50).

9. The data acquisition method according to claim 1, wherein the scanner head (50) defines a scanning plane (76) with its optical deflection element (56) and its movement direction (75), the scanner head (50) comprising a scale (77), which is situated at a distance to a linear measuring system (78) of the laser scanner (1) and in this scanning plane (76).

10. The data acquisition method according to claim 1, wherein the scanner head (50) comprises a scale (77), which is situated at least in proximity to a main plane (107) of the first objective (57).

11. The data acquisition method according to claim 1, wherein the scanner apparatus (72) comprises a counter oscillator (73), which is fastened so it is displaceable on a linear guide and has a connecting rod attachment point (69'), which is connected via a connecting rod (70') to the drive (71) of the scanner apparatus (72).

12. The data acquisition method according to claim 1, wherein the sample plane (49) is situated essentially horizontally.

13. The data acquisition method according to claim 1, wherein the movement direction (75) of the scanner head (50) defines an X axis or scanning axis of a Cartesian coordinate system and the sample table (2) is moved linearly in a Y direction situated perpendicularly thereto.

14. The data acquisition method according to claim 1, wherein two laser beams (54, 55) of different wavelengths, which are oriented parallel to one another and run parallel to the sample plane (49), are provided using the at least one laser (51, 52) and the first optical system (53) and deflected toward the sample using an optical deflection element (56) of a scanner apparatus (72).

15. The data acquisition method according to claim 14, wherein these laser beams (54, 55) are focused on the sample in the plane (49) using the first objective (57), after which the emission beam bundles (59, 60) of different wavelengths, which are triggered by the laser beams (54, 55) and are deflected by the first objective (57) and the deflection element (56) in a direction essentially parallel to the plane (49), are conducted using the second optical system (58) to two detectors (61, 61') and acquired by these detectors (61, 61').

16. The data acquisition method according to claim 15, wherein a wedge-shaped dichroic mirror (62) having front and rear dichroic surfaces (63, 64), which are situated at an intermediate angle (â) to one another, is used as part of the optical deflection element (56), the wedge-shaped dichroic mirror (62) being set so that the two laser beams (54, 55) are each reflected on one of the surfaces (63, 64), and the wedge-shaped dichroic mirror (62) causing a spatial separation of the two resulting focal points (65) and of the two emission beam bundles (59, 60) deflected in the direction of the detectors (61, 61') by the intermediate angle ($\beta$).

17. The data acquisition method according to claim 16, wherein the deflection of the scanner head (50) in the X axis (75) is measured using a scale (77), which is situated at a distance to a linear measuring system (78) of the laser scanner (1) in this scanning plane (76).

18. The data acquisition method according to claim 16 wherein the deflection of the scanner head (50) in the X axis (75) is measured using a scale (77), which is situated at least in proximity to the main plane (107) of the first objective (57).

19. The data acquisition method according to claim 15, wherein an optical deflection element (56) implemented as a pentamirror configuration (66) having a wedge-shaped dichroic mirror (62) and a single mirror (67) is used, this pentamirror configuration (66) correcting tilts of the scanner head (50) around a Y axis running perpendicular to the scanning axis (75) so that the resulting focal points (65) do not change their current position in the sample plane (49).

* * * * *